United States Patent [19] [11] 3,969,515
Argoudelis et al. [45] July 13, 1976

[54] ANTIBIOTIC U-48,266
[75] Inventors: Alexander D. Argoudelis; Fritz Reusser, both of Portage, Mich.
[73] Assignee: The Upjohn Company, Kalamazoo, Mich.
[22] Filed: Mar. 10, 1975
[21] Appl. No.: 556,573

[52] U.S. Cl. .................................................. 424/118
[51] Int. Cl.² ........................................ A61K 35/74
[58] Field of Search ...................................... 424/118

[56] References Cited
UNITED STATES PATENTS
3,824,305 7/1974 Hamill et al. ........................ 424/118

Primary Examiner—Jerome D. Goldberg
Attorney, Agent, or Firm—Roman Saliwanchik

[57] ABSTRACT

New antibiotic U-48,266 produced by the controlled fermentation of the microorganism *Streptomyces ficellus* Dietz, sp. n., NRRL 8067. This antibiotic and its acid and base addition salts are active against Gram-positive and Gram-negative bacteria. Accordingly, they can be used in various environments to eradicate or control such bacteria.

2 Claims, 4 Drawing Figures

ANTIBIOTIC U-48,266

BRIEF SUMMARY OF THE INVENTION

The novel antibiotic of the invention, U-48,266 is obtained by culturing *Streptomyces ficellus* Dietz, sp. n., NRRL 8067, in an aqueous nutrient medium under aerobic conditions. Antibiotic u-48,266 and its acid and base addition salts have the property of adversely affecting the growth of Gram-positive bacteria, for example, *Staphylococcus aureus*, *Sarcina lutea*, *Bacillus subtilis*, and Gram-negative bacteria, for example, *Escherichia coli*, *Salmonella gallinarum*, *Klebsiella pneumoniae*, and *Proteus vulgaris*. Accordingly, U-48,266 and its acid and base addition salts can be used alone or in combination with other antibiotic agents to prevent the growth of or reduce the number of bacteria, as disclosed above, in various environments.

DETAILED DESCRIPTION OF THE INVENTION

Chemical and Physical Properties of U-48,266

Molecular Formula: $C_{17}H_{25}N_7O_5$ (Determined by high resolution mass spectrometry)

Elemental Analysis: Calcd.: C, 50.16; H, 6.19; N, 24.09; O, 19.66.

Molecular Weight: 407.3498 (Determined by mass spectrometry)

Melting Point: Melts with decomposition over a broad range.

Specific Rotation: $[\alpha]_D^{25} = -6.6°$ (c, 1, water)

Solubilities: Antibiotic U-48,266 is soluble in water and lower alcohols, for example, methanol and ethanol; it is relatively insoluble in ketones, halogenated or saturated hydrocarbon solvents, ethyl acetate, or other ester-type solvents.

| Ultraviolet Absorption Spectra: Solvent | λ Max in mμ, | a |
|---|---|---|
| Water | 259 | 0.49 |
|  | 265 | 0.47 |
|  | 320 | (sh) 0.18 |

Titration Data:
a. In water, using aqueous hydrochloric acid as titrant: pKa' 8.7, eq. weight 210.
b. In water, using aqueous potassium hydroxide as titrant: pKa' 8.2, eq. weight 241.

Figure 1:
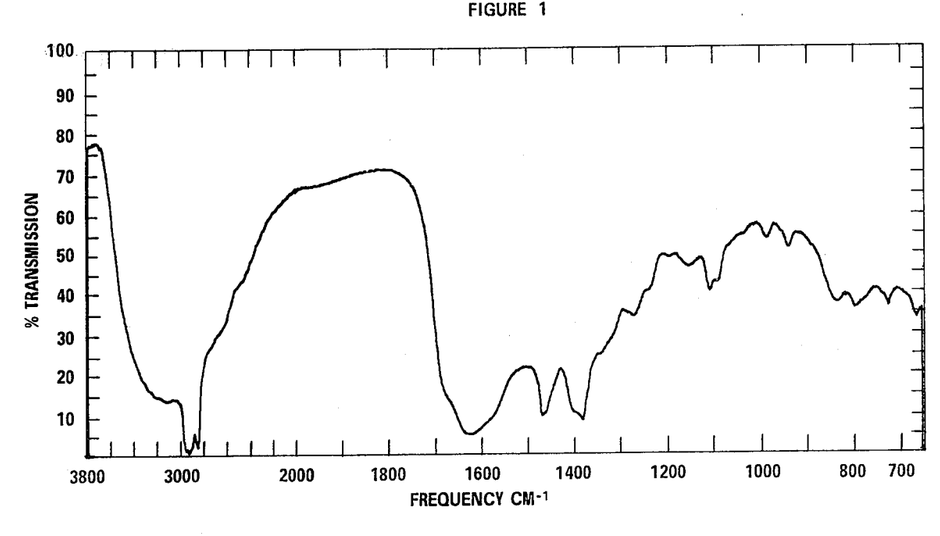

Infrared Absorption Spectra: U-48,266 has a characteristic infrared absorption spectrum in a mineral oil mull as shown in FIG. 1 of the drawings. Peaks are observed at the following wave lengths expressed in reciprocal centimeters:

| Band Frequency (Wave Numbers) | Intensity | |
|---|---|---|
| 3130 | s | |
| 2960 | s, oil | |
| 2920 | s, oil | |
| 2850 | s, oil | |
| 1622 | s | |
| 1465 | s, oil | |
| 1393 | s, sh | (sh=shoulder) |
| 1378 | s, oil | |
| 1338 | m | |
| 1268 | m | |
| 1238 | m, sh | |
| 1150 | m | |
| 1105 | m | |
| 1088 | m, sh | |
| 983 | w | |
| 938 | w | |
| 833 | m | |
| 792 | m | |
| 721 | m, oil | |
| 660 | m | |

U-48,266 also has a characteristic infrared absorption spectrum when pressed in a KBr disc. Peaks are observed at the following wave lengths expressed in reciprocal centimeters:

| Band Frequency (Wave Numbers) | Intensity |
|---|---|
| 3380 | s |
| 3220 | s |
| 3130 | s |
| 2980 | s |
| 2880 | s |
| 1625 | s |
| 1392 | s |
| 1340 | s, sh |
| 1268 | m |
| 1235 | m |
| 1142 | m |
| 1103 | m |
| 1088 | m |
| 982 | m |
| 937 | m |
| 832 | m |
| 791 | m |
| 660 | m |

Infrared band intensities, throughout this disclosure, are indicated as *s*, *m*, and *w* respectively, and are approximated in terms of the backgrounds in the vicinity of the bands. An *s* band is of the same order of intensity as the strongest in the spectrum; *m* bands are between one-third and two-thirds as intense as the strongest band; and, *w* bands are less than one-third as intense as the strongest band. These estimates are made on the basis of a percent transmissions scale.

Nuclear Magnetic Resonance (NMR)

Figure 2:
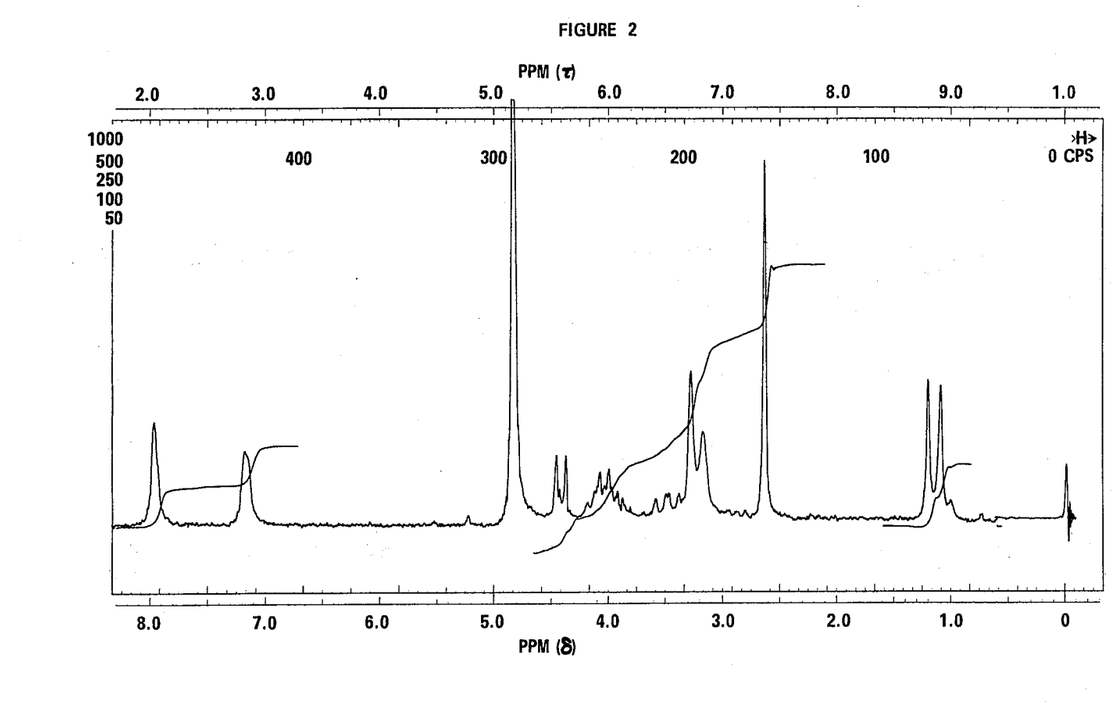

The NMR spectrum of antibiotic U-48,266 at 60 megacycles is shown in FIG. 2 of the drawings. The NMR spectrum was observed on a Varian A-60 Spectrometer on a solution (ca. 0.5 ml., ca. 15% concentration) of the sample of U-48,266 in deuterium oxide ($D_2O$). The spectrum was calibrated against internal tetramethylsilane and the precision of the Δ γ was >±1c.p.s. Frequencies were recorded in c.p. s. downfield from tetramethylsilane.

Thin Layer Chromatography (TLC)

Figure 3:
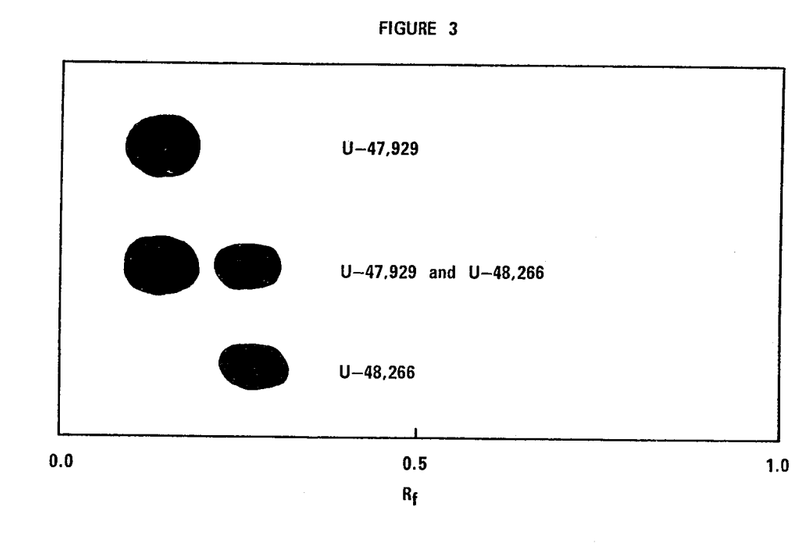

Antibiotic U-48,266 has a typical TLC in comparison with antibiotic U-47,929 as shown in FIG. 3 of the drawings. The conditions of the TLC test are as follows:

Silica gel plates are used as support and 95% ethanol-water (75:25 v/v) is the solvent system. Antibiotic U-48,266 is detected by bioautography on S. lutea-seeded agar trays. Antibiotic U-47,929 is detected by bioautography on S. aureus - seeded agar trays.

| Antibacterial Activity of U-48,266 in Agar* | | | |
|---|---|---|---|
| | Zone of Inhibition (mm) | | |
| Organism | 10 mg/ml | 5 mg/ml | 1 mg/ml |
| E. coli (synthetic)[1] | 30 (vl) | 24 (vl) | 18 (vl) |
| E. coli | 28 (vl) | 26 (vl) | 22 (vl) |
| P. vulgaris (synthetic)[2] | 0 | 0 | 0 |

| | | | |
|---|---|---|---|
| K. pneumoniae | 36 (l.) | 34 (l.) | 31 (l.) |
| B. cereus | 0 | 0 | 0 |
| S. lutea | 37 (l.) | 33 (l.) | 26 (l.) |
| P. oxalicum | 0 | 0 | 0 |
| Ps. aeruginosa | 0 | 0 | 0 |
| S. gallinarum | 31 (vl) | 29 (vl) | 26 (vl) |
| B. subtilis (synthetic)[3] | 16.5 | traces | 0 |
| B. subtilis | 42 (vl) | 38 (vl) | 25 (vl) |
| S. lutea[4] | 48 | 46 | 40 |
| P. rettgeri (synthetic)[5] | 0 | 0 | 0 |
| S. aureus | 19 (l.) | 0 | 0 |
| M. avium | 44 (vl) | 0 | 0 |
| P. Vulgaris | 38 (vl) | 36 (vl) | 28 (vl) | vl = very light zone    l = light zone

*0.08 ml aliquots of test solution were applied on 12.5 mm paper discs and the discs were applied on agar trays seeded with the appropriate organisms.

[1] E. coli (synthetic) agar

| | | |
|---|---|---|
| $KH_2PO_4$ | 3 | g/liter |
| $K_2HPO_4$ | 7 | g/liter |
| $MgSO_4$ | 0.1 | g/liter |
| $(NH_4)_2SO_4$ | 1 | g/liter |
| Sodium citrate | 1 | g/liter |
| Glucose.$H_2O$ | 2 | g/liter |
| Agar | 15 | g/liter |

[2] P. vulgaris (synthetic) agar
Same as E. coli (synthetic) above, plus 10 ml of BME vitamin mixture, 100X, per liter. BME vitamin mixture, 100X is supplied by Microbiological Associates, Inc., Bethesda, Maryland.

[3] B. subtilis (synthetic) agar

| | | |
|---|---|---|
| $Na_2HPO_4.7H_2O$ | 1.7 | g/liter |
| $KH_2PO_4$ | 2 | g/liter |
| $(NH_4)_2SO_4$ | 1 | g/liter |
| $MgSO_4$ | 0.1 | g/liter |
| Glucose.$H_2O$ | 2 | g/liter |
| Agar | 15 | g/liter |

[4] S. lutea agar
Complex nutrient agar (Difco, Antibiotic Medium 2) adjusted to pH 8.5 with NaOH prior to sterilization. Post-sterilization pH = ca. 8

[5] P. rettgeri (synthetic) agar
Identical with E. coli (synthetic) agar.

Chemical and Physical Properties of U-48,266 HCl

Molecular Formula: $C_{17}H_{25}N_7O_5.2HCl$
Elemental Analysis: Found: C, 38.04; H, 5.86; N, 18.42; Cl, 16.04.
Melting Point: Melts with decomposition over a broad range.
Specific Rotation: $[\alpha]_D^{25} = +12°$ (c, 1, water)
Solubilities: Same as for antibiotic U-48,266 "free base".

Ultraviolet Absorption Spectra:

| Solvent | λ Max in mμ, a | |
|---|---|---|
| Water | 265 | 1.65 |

Figure 4:
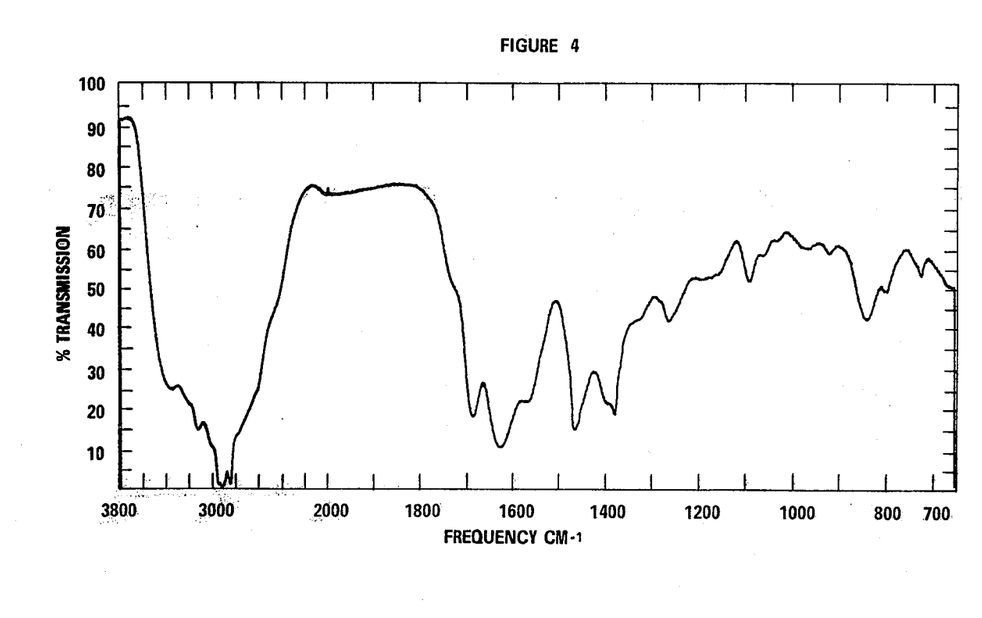

Infrared Absorption Spectra: Antiobiotic U-48,266 HCl has a characteristic infrared absorption spectrum in a mineral oil mull as shown in FIG. 4 of the drawings. Peaks are observed at the following wave lengths expressed in reciprocal centimeters:

| Band Frequency (Wave Numbers) | Intensity |
|---|---|
| 3370 | s |
| 3210 | s, sh |
| 3130 | s |
| 3010 | s, sh |
| 2960 | s, oil |
| 2920 | s, oil |
| 2850 | s, oil |
| 2620 | s, sh |
| 2440 | m, sh |
| 1725 | m, sh |
| 1685 | s |
| 1625 | s |
| 1568 | s |
| 1465 | s, oil |
| 1392 | s |
| 1378 | s, oil |
| 1330 | m, sh |
| 1262 | m |
| 1192 | w |
| 1170 | w, sh |
| 1155 | w, sh |
| 1090 | w |
| 1060 | w |
| 1030 | w |
| 965 | w |
| 918 | w |
| 838 | m |
| 795 | m |
| 720 | w, oil |

Antibiotic U-48,266 HCl has a characteristic infrared absorption spectrum when pressed in a KBr disc. Peaks are observed at the following wave lengths expressed in reciprocal centimeters:

| Band Frequency (Wave Numbers) | Intensity |
|---|---|
| 3410 | s |
| 3200 | s, sh |
| 3130 | s |
| 3020 | s |
| 2850 | s |
| 2790 | s, sh |
| 2620 | s, sh |
| 2440 | m, sh |
| 1725 | m, sh |
| 1685 | s |
| 1625 | s |
| 1565 | s |
| 1468 | s |
| 1430 | s, sh |
| 1395 | s |
| 1330 | m |
| 1260 | m |
| 1190 | m |
| 1160 | m, sh |
| 1088 | m |
| 1060 | w, sh |
| 1028 | w, sh |
| 970 | w |
| 918 | w |
| 835 | m |
| 795 | m |
| 735 | w |

Comparison Of The Antibacterial Activity Of Antibiotic U-48,266 free base And Antibiotic U-48,266 HCl

| Antibiotic | Zone (mm) | | | | | |
|---|---|---|---|---|---|---|
| | 10 | 5 | 2.5 | 1.25 | 0.625 | (mg/ml) |
| U-48,266 free base | 51 | 49 | 45 | 43 | 41 | |
| U-48,266 HCl | 51 | 49 | 47 | 45 | 43 | |

The test is an agar diffusion test as disclosed previously for determining the antibiotic activity of antibiotic U-48,266. The organism in this comparison test is *Sarcina lutea*.

THE MICROORGANISM

The microorganism used for the production of U-48,266 is *Streptomyces ficellus* Dietz, sp. n., NRRL 8067. A subculture of this microorganism can be obtained from the permanent collection of the Northern Regional Research Laboratory, U.S. Department of Agriculture, Peoria, Ill. U.S.A.

The microorganism of this invention was studied and characterized by Ms. Alma dietz of the Upjohn Research Laboratory. The taxonomy of *Streptomyces ficellus* Dietz. sp. n., NRRL 8067, is disclosed on pgs. 7–17 of co-pending U.S. application Ser. No. 542,226, filed on Jan. 20, 1975.

The new compound of the invention is produced when the elaborating organism is grown in an aqueous nutrient medium under submerged aerobic conditions. It is to be understood, also, that for the preparation of limited amounts surface cultures and bottles can be employed. The organism is grown in a nutrient medium containing a carbon source, for example, an assimilable carbohydrate, and a nitrogen source, for example, an assimilable nitrogen compound of proteinaceous material. Preferred carbon sources include glucose, brown sugar, sucrose, glycerol, starch, cornstarch, lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distillers' solids, animal peptone liquors, meat and bone scraps, and the like. Combinations of these carbon and nitrogen sources can be used advantageously. Trace metals, for example, zinc, magnesium, manganese, cobalt, iron, and the like, need not be added to the fermentation media since tap water and unpurified ingredients are used as components of the medium prior to sterilization of the medium.

Production of the compound of the invention can be effected at any temperature conducive to satisfactory growth of the microorganism, for example, between about 18° and 40°C., and preferably between about 20° and 28°C. Ordinarily, optimum production of the compound is obtained in about 3 to 15 days. The medium normally remains neutral during the fermentation. The final pH is dependent, in part, on the buffers present, if any, and in part on the initial pH of the culture medium.

When growth is carried out in large vessels and tanks, it is preferable to use the vegetative form, rather than the spore form, of the microorganism for inoculation to avoid a pronounced lag in the production of a new compound and the attendant inefficient utilization of the equipment. Accordingly, it is desirable to produce a vegetative inoculum in a nutrient broth culture by inoculating this broth culture with an aliquot from a soil stock, an agar plug stored above liquid $N_2$, or a slant culture. When a young, active vegetative inoculum has thus been secured, it is transferred aseptically to large vessels or tanks. The medium in which the vegetative inoculum is produced can be the same as, or different from, that utilized for the production of the new compound, so long as good growth of the microorganism is obtained.

A variety of procedures can be employed in the isolation and purification of the compound of the subject invention, for example, solvent extraction, partition chromatography, silica gel chromatography, liquid-liquid distribution in a Craig apparatus, adsorption on resins, and crystallization from solvents.

In a preferred recovery process the compound of the subject invention is recovered from the culture medium by separation of the mycelia and undissolved solids by conventional means, such as by filtration or centrifugation. The antibiotic is recovered from the filtered or centifuged broth by passing the broth over an adsorbent, advantageously a highly selective magnesia-silica gel adsorbent, for example, florisil which is sold by The Floridin Company, Pittsburg, Pa. The adsorbent is eluted with a suitable solvent, for example a lower alkanone, advantageously, acetone. Fractions containing the desired antibiotic U-48,266, as determined by thin layer chromatography (tlc) and antibacterial assays, as hereinafter described, are concentrated and freeze-dried to give a crude preparation of antibiotic U-48,266. Such crude preparations of antibiotic U-48,266 can be used where purity of the antibiotic preparation is not critical, for example, as a feed supplement.

The antibiotic of the subject invention also can be recovered from fermentation broth by filtration followed by adsorption on alumina (neutral or acid washed) and elution with water-acetone mixtures. Further, U-48,266 can be recovered from fermentation broth by resin sorption on a resin comprising a nonionic macro porous copolymer of styrene cross linked with divinylbenzene. Suitable resins are Amberlite XAD-2 and XAD-4, accordingly to the procedure disclosed in U.S. Pat. 3,515,717. (Amberlite resins are available from Rohm and Haas, Philadelphia, Pa.). The antibiotic can be eluted from said resin by a water-lower alcohol (preferably methanol) mixture or a water-acetone mixture.

Since antibiotic U-48,266 is an amphotermic substance, both cation and anion exchange resins can be used for its isolation from the clear filtrates of an antibiotic U-48,266 fermentation beer.

Essentially antibiotic U-48,266 can be obtained from crude preparations, obtained as disclosed above, by chromatographic procedures. In a preferred process, crude preparations of antibiotic U-48,266 are first subjected to chromatographic procedures using a nonionic macro porous copolymer of styrene crosslinked with divinylbenzene resin, for example, Amberlite XAD-4. The column is eluted with water and fractions are tested for bioactivity against *S. aureus* and *Sarcina lutea*. Fractions are also analyzed by tlc on silica gel using 95 percent aqueous ethanol-water (75:25 v/v) as the solvent. Antibiotic U-48,266 is located by spraying the silica gel plates with a ninhydrin solution. Active fractions are combined and subjected to chromotography on a cationic exchange resin to remove inorganic salts. Suitable cationic exchange resins are carboxylic acid ion exchange resins, for example, IRC-50 in the hydrogen ion form, which is supplied by Rohm and Haas Company, Philadelphia, Pa. Another suitable resin is a porous decolorizing resin containing phenolic polar substituents, for example, Duolite S-30 sold by The Chemical Process Company, Redwood City, Cal.

The cationic chromatography column is eluted with a base, for example, $NH_4OH$, and active fractions are tested for bioactivity against the microorganisms *S. lutea*. Active fractions are then subjected to silica gel chromotography for further purification. The silica gel column is eluted with a solvent system consisting of 95 percent aqueous ethanol-water (75:25 v/v). Active fractions are determined by activity against the microorganisms *S. lutea*. Such active fractions are combined and freeze-dried. Further purification of these preparations of antibiotic U-48,266 is obtained by treatment with activated carbon. The preparations from the silica gel column are dissolved in water and mixed with the activated carbon. The filtrate is then freeze-dried to given an essentially pure preparation of antibiotic U-48,266.

Since antibiotic U-48,266 is an amphoteric substance, it can form salts with both acids and bases. Examples of inorganic and organic acids which can be used to form salts with antibiotic U-48,266, but which examples should not be considered limiting, are hydrochloric, sulfuric, phosphoric, acetic, succinic, citric, lactic, maleic, fumaric, pamoic, cholic, palmitic, mucic, camphoric, glutaric, glycolic, phthalic, tartaric, lauric, stearic, salicylic, 3-phenylsalicyclic, 5-phenylsalicyclic, 3-methylglutaric, orthosulfobenzoic, cyclohexanesulfamic, cyclopentanepropionic, 1,2-cyclohexanedicarboxylic, 4-cyclohexenecarboxylic, octadecenylsuccinic, octenylsuccinic, methanesulfonic, benzenesulfonic, helianthic, Reinecke's, dimethyldithiocarbamic, sorbic, monochloroacetic, undecylenic, 4'-hydroxyazobenzene-4-sulfonic, octadecylsulfuric, picric, benzoic, cinnamic, and like acids.

Salts of antibiotic U-48,266 also can be formed with inorganic or organic bases. Such salts can be prepared, as for example, by dissolving antibiotic U-48,266 in water, adding a dilute base until the pH of the solution is about 10.0 to 11.0, and freeze-drying the solution to provide a dried residue consisting of the U-48,266 salt. Antibiotic U-48,266 salts with inorganic cations which can be formed include the sodium, potassium, and calcium salts. Other salts of U-48,266, including those with inorganic bases such as primary, secondary, and tertiary monoamines as well as with polyamines, also can be formed using the above-described or other commonly employed procedures. Other valuable salts are obtained with therapeutically effective bases which impart additional therapeutic effects thereto. Such bases are, for example the purine bases such as theophyllin, theobromin, caffeine, or derivatives of such purine bases; antihistaminic bases which are capable of forming salts with weak acids; pyridine compounds such as nicotinic acid amide, isonicotinic acid hydrazide, and the like; phenylalkylamines such as adrenaline, ephedrine, and the like; choline, and others. Salts of U-48,266 can be used for the same biological purposes as the parent compound.

Antibiotic U-48,266 and its salts are active against *S. aureus* and can be used to disinfect washed and stacked food utensils contaminated with this bacteria; they can also be used as disinfectants on various dental and medical equipment contaminated with *S. aureus*. Further, antibiotic U-48,266 and its salts can be used to treat laboratory mice infected with *S. aureus*. Still further, antibiotic U-48,266 and its salts can be used as a bacteriostatic rinse for laundered clothes, and for impregnating papers and fabrics; and, they are also useful for suppressing the growth on sensitive organisms in plate assays and other microbiological media.

It is to be understood that the microbiological process disclosed herein, though described in detail with reference to *Streptomyces ficellus* Dietz. sp. n., NRRL 8067, is not limited to this particular microorganism deposit. It is intended that any microorganism meeting the cultural characteristics disclosed herein, or substantial equivalence thereof, wherever deposited in the world, is a part of the subject microbiological process.

The following examples are illustrative of the process and products of the subject invention but are not to be construed as limiting. All percentages are by weight and all solvent mixture proportions are by volume unless otherwise noted.

EXAMPLE 1

Part A. Fermentation

A soil stock of *Streptomyces ficellus* Dietz, sp. n., NRRL 8067, is used to inoculate a series of 500-ml. Erlenmeyer flasks, each containing 100 ml. of sterile preseed medium consisting of the following ingredients:

| | |
|---|---|
| Glucose monohydrate | 25 g/liter |
| Pharmamedia* | 25 g/liter |
| Tap water q.s. | 1 liter |

*Pharmamedia is an industrial grade of cottonseed flour produced by Traders Oil Mill Company, Fort Worth, Texas.

The pressed medium presterilization pH is 7.2. The preseed inoculum is grown for three days at 28° C. on a Gump rotary shaker operating at 250 r.p.m. and having a 2 ½ inch stroke.

Preseed inoculum (300 ml.), prepared as described above, is used to inoculate a seed tank containing 20 liters of sterile seed medium consisting of the following ingredients:

| | |
|---|---|
| Glucose monohydrate | 10 g/liter |
| Corn steep liquor | 10 g/liter |
| Pharmamedia | 2 g/liter |
| Wilson's Peptone Liquor No. 159* | 10 g/liter |
| Tap water | Balance |

*Wilson's Peptone Liquor No. 159 is a preparation of hydrolyzed proteins of animal origin.

The inoculated seed medium is incubated at a temperature of 28° c. for 2 days while being agitated at a rate of 400 r.p.m. and aerated at a rate of 10 standard liters per minute with a back pressure of 10 psig.

After 2 days incubation, the seed medium is used to inoculate (the inoculation rate is 5 liters of seed inoculum per 100 liters of fermentation medium) a 250 liter tank fermentation containing sterile fermentation medium consisting of the following ingredients:

| | |
|---|---|
| Glucose monohydrate | 15 g/liter |
| Black strap Molasses | 20 g/liter |
| Starch | 40 g/liter |
| Pharmamedia | 25 g/liter |
| CaCO$_3$ | 8 g/liter |
| Tap water q.s. | Balance |
| PH – 7.2 (presterilization) | |

The fermentation tank is incubated at a temperature of 28° C., with agitation of 240 r.p.m. and aeration at 80 standard liters per minute with back pressure at 10 psig. Ucon antifoam agent (a synthetic defoamer supplied by Union Carbide, N.Y., N.Y.) is used if needed. Harvest is usually after 3 to 12 days of fermentation. A typical 3-day fermentation has the following titers of antibiotic in the fermentation broth:

| Day | Assay, BU/ml. |
|---|---|
| 1 | 0 |
| 2 | <1 |
| 3 | 2.6 |

| Day | Assay, BU/ml. |
|---|---|
| 4 | 4 |

The assay is a disc plate assay using *S. lutea* as the test organism. It is conducted with complex nutrient agar (Difco, antibiotic medium 2) adjusted to pH 8.5 with aqueous NaOH prior to sterilization. Post-sterilization pH, ca. 8.0. A unit volume (0.08 ml) of solution containing the substance to be assayed is placed on a 12.7 mm paper disc which is then placed on an agar plate seeded with the assay organism. The agar plate is then incubated for 16 to 18 hours at 37° C. A biounit (BU) is defined as the concentration of the antibiotic which gives a 20 mm zone of inhibition under the standard assay conditions. Thus, if for example a fermentation beer has to be diluted 1/100 to give a 20 mm zone of inhibition, the potency of such beer is 100 BU/ml.

Part B. Recovery

Antibiotic U-48,266 in beers is detected and assayed by the use of tlc and antibacterial assays. Thin layer chromatograms are run on silica gel plates using 95% aqueous ethanol-water (75:25 v/v) as the solvent system. Bioactivity is detected by bioautography using *S. lutea*-seeded agar trays and the assay procedure disclosed in Example 1, Part A.

Whole fermentation beer (ca. 5000 liters), obtained as described above, is filtered with the aid of diatomaceous earth as a filter aid. The filter cake is washed with water and the cake is then discarded. Part of the filtered beer (1900 liters) is passed at a rate of 5 liters/min. over a florisil column prepared from ca. 80 kg. of acid-washed florisil. The spent beer is discarded. The column is then washed with 150 liters of water at a rate of 5 liters/min. The aqueous wash is concentrated in vacuo to a volume of ca. 40 liters, and this concentrate is freeze-dried to give 515 grams of a crude preparation of antibiotic U-48,266 which is designated Preparation A.

The florisil column is then eluted with 900 liters of 50% aqueous acetone. The following fractions are obtained:

| | | |
|---|---|---|
| Fraction I | — | 35 liters |
| Fraction II | — | 40 liters |
| Fraction III | — | 225 liters |
| Fraction IV | — | 225 liters |

Fraction I is concentrated to an aqueous and freeze-dried to give 103 grams of a preparation of antibiotic U-48,266 which is designated Preparation B.

Fraction II is concentrated to an aqueous freeze-dried to give 240 grams of a preparation of antibiotic U-48,266 which is designated Preparation C.

Fractions III and IV, which contain antibiotic U-47,929, are not processed further for antibiotic U-48,266.

Preparations A, B, and C, obtained as described above, are combined and then subjected to further purification procedures as disclosed in Part C.

Part C. Purification (No. 1) Chromatography on Amberlite XAD-4

The starting material is Preparation A (515 grams), Preparation B (103 grams), and Preparation C (240 grams), obtained as described above in Part B. These preparations are combined and dissolved in 9 liters of 10% aqueous sodium chloride solution. This solution is adjusted to pH 10.0 with 5N aqueous sodium hydroxide and the resulting solution is clarified by filtration by using filter aid. The filter cake is washed with 1 liter of 10% aqueous sodium chloride. The wash is combined with the filtrate and this solution is used for the chromatography.

The Amberlite XAD-4 which is used in the chromatography is purified as follows: Amberlite XAD-4 (ca. 9 liters) is washed (batchwise) with:

1. 9 liters of water,
2. 9 liters of 50% aqueous acetone,
3. 9 liters of acetone,
4. 9 liters of methanol, and
5. 9 liters of 50% aqueous methanol.

The resin is then transferred to a column and the column is washed with 50 liters of water (flow rate: 100–150 ml/min).

The column is prepared from 9 liters of washed Amberlite XAD-4, as described above, by pouring the resin into the water-filled column and allowing the resin to settle under atmospheric pressure.

The combined filtrate-wash starting material, prepared as described above, is passed through the column at a rate of ca. 10 ml/min. The spent beer is collected in two equal fractions designated Spent-1 and Spent-2. The column is then eluted with water. Eight fractions are collected. To monitor column effluents, bioactivity vs. *S. lutea* or *S. aureus* is determined as follows: Filter discs (12.7 mm diameter) are dipped into the column eluates (1 disc/fraction) and the dried discs are then placed on agar plates seeded with *S. lutea* or *S. aureus*. The plates are incubated for 16 to 18 hours at 37° C. The resulting zones of inhibition (measured in mm diameter) are used as an indication of bioactivity contained in the fractions. The activity of the starting material, Spent-1, Spent-2, and the aqueous fractions as well as the volume of the obtained fractions are listed below:

| | Volume (l.) | Zones (mm) *S. aureus* | *S. Lutea* |
|---|---|---|---|
| Starting Material | 10 | 33.5 | 40 |
| Spent-1 | 5 | 0 | 0 |
| spent-2 | 5 | 0 | 0 |
| Water-1 | 2 | 0 | traces |
| -2 | 2 | 0 | 25 |
| -3 | 1 | 18 (very light) | 31 |
| -4 | 4 | 22 | 42 |
| -5 | 8 | 21 | 34 |
| -6 | 2 | 0 | 28 |
| -7 | 2 | traces | 23 |
| -8 | 2 | traces | 22 |

Spent-1, Spent-2 and water fractions 1, 2, 7 and 8 are discarded.

The above fractions are analyzed by tlc and bioassay. Fractions 3, 4, 5, and 6 are combined and used for the IRC-50 (H+) chromatography described below.

(No. 2) Chromatography on IRC (H+) Chromatography to Remove Inorganic Salts

The column is prepared from 2 liters of IRC-50 in the hydrogen form (internal diameter of column is 10.5 cm.).

The pool (ca. 16 liters, pH 10.0) obtained by a combination of fractions 3, 4, 5, and 6 of the Amberlite XAD-4 chromatography, as described above, is passed through the column at a rate of 20 ml/min. The spent beer is collected in four fractions designated S-1, S-2, S-3 and S-4. The column is washed with 5 liters of water at a rate of 20 ml/min.

Spent-1 and Spent-2 are combined and the bioactivity present in these fractions is recovered by another IRC-50 (H+) chromatography, described infra.

The column is then eluted with 5 liters of 0.25N NH₄OH (rate 20 ml/min.) which is collected as one fraction. The column is then eluted with 1N NH₄OH (rate 10 ml/min.). Fractions of 20 ml are collected. Testing gives the following results:

| Fraction No. | Zone (mm) S. lutea |
|---|---|
| 0.25N NH₄OH | 0 |
| 1N NH₄OH | |
| 5 | 0 |
| 10 | 0 |
| 15 | 0 |
| 220 | 0 |
| 225 | 22 |
| 230 | 28 |
| 235 | 32 |
| 240 | 32 |
| 245 | 33 |
| 250 | 34 |
| 255 | 35 |
| 260 | 37 |
| 265 | 38 |
| 270 | 38 |
| 275 | 39 |
| 280 | 39 |
| 290 | 41 |
| 300 | 42 |
| 310 | 41 |
| 320 | 41 |
| 330 | 40 |
| 340 | 40 |
| 350 | 40 |
| 360 | 42 |
| 370 | 44 |
| 380 | 49 |
| 390 | 43 |
| 400 | 37 |
| 410 | 22 |
| 420 | 18 |
| 430 | 17 |
| 440 | traces |
| 450 | traces |
| 460 | 0 |
| 470 | 0 |
| 480 | 0 |
| 490 | 0 |
| 500 | 0 |

Fractions 225–410 are combined and freeze-dried to give 14.74 grams of a preparation of antibiotic U-48,266 designated ADA-55.1.

Spent-1 and Spent-2, obtained in the IRC-50 chromatography described above, are found to contain bioactive material(s) against *S. lutea*.

The two fractions are combined (8 liters) and passed through a column containing 1 liter of IRC-50 in the hydrogen form. The spent is discarded. The column is washed with 2 liters of water and the wash is discarded. The column is eluted with 2 liters of 0.25N NH₄OH which is also discarded. Lastly, the column is eluted with 1N NH₄OH. Fractions of 20 ml are collected. Testing gives the following results:

| Fraction No. | Zone(mm) S. lutea |
|---|---|
| 10 | 0 |
| 20 | 0 |
| 180 | 0 |
| 190 | traces |
| 200 | 32 |
| 210 | 37 |
| 220 | 39 |
| 230 | 40 |
| 240 | 42 |

-continued

| Fraction No. | Zone(mm) S. lutea |
|---|---|
| 250 | 42 |
| 260 | 42 |
| 270 | 42 |
| 280 | 43 |
| 290 | 45 |
| 300 | 37 |
| 310 | 22 |
| 320 | traces |
| 330 | 0 |
| 340 | 0 |
| 350 | 0 |

Fractions 195–300 are freeze-dried to give 3.19 grams of a preparation of antibiotic U-48,266 which is designated ADA-58.1.

(No. 3) Silica Gel Chromatography

The column is prepared from 1.8 kg. of silica gel packed in the solvent consisting of 95% aqueous ethanol-water (75:25 v/v).

The starting material, 14 grams of Preparation ADA-55.1 is dissolved in 50 ml of water. The solution is adjusted to Ph 10.0 and mixed with 100 grams of silica gel and 150 ml of 95% aqueous ethanol. The mixture is concentrated to dryness. The resulting dry powder is used on the top of the column and the column is then eluted with the solvent system described above. Fractions of 20 ml are collected at a rate of 8–10 ml/min. Testing shows the following results:

| Fraction No. | Zone (mm) S. lutea |
|---|---|
| 10 | 0 |
| 20 | 0 |
| 340 | 0 |
| 350 | 17 |
| 360 | 20 |
| 370 | 20 |
| 380 | 20 |
| 390 | 19 |
| 400 | 18 |
| 410 | 18 |
| 420 | traces |
| 430 | traces |
| 440 | 0 |
| 450 | 18 |
| 460 | 18 |
| 470 | 18 |
| 480 | 20 |
| 490 | 21 |
| 500 | 20 |
| 510 | 22 |
| 520 | 24 |
| | New tray |
| 530 | 22 |
| 540 | 22 |
| 550 | 22 |
| 560 | 25 |
| 570 | 27 |
| 580 | 26 |
| 590 | 29 |
| 600 | 28 |
| 610 | 29 |
| 620 | 29 |
| 630 | 29 |
| 640 | 30 |
| 650 | 30 |
| 660 | 31 |
| 670 | 33 |
| 680 | 36 |
| | New tray |
| 690 | 39 |
| 700 | 41 |
| 710 | 41 |
| 720 | 41 |
| 730 | 41 |
| 740 | 41 |
| 750 | 42 |
| 760 | 43 |
| 770 | 43 |
| 780 | 42 |
| 790 | 43 |

| Fraction No. | Zone (mm) S. lutea | |
|---|---|---|
| 800 | 42 | |
| 810 | 42 | |
| 820 | 42 | |
| 830 | 42 | |
| 840 | 41 | |
| 850 | 41 | |
| 860 | 41 | |
| 870 | 40 | |
| 880 | 38 | |
| 890 | 39 | |
| 900 | 37 | |
| 910 | 38 | |
| 920 | 37 | |
| 930 | 36 | |
| 940 | 35 | |
| 950 | 34 | |
| 960 | 34 | |
| 970 | 34 | |
| 980 | 33 | |
| 990 | 32 | |
| 1000 | 31 | |
| 1010 | 30 | |
| 1020 | 29 | |
| 1030 | 29 | |
| | | New tray |
| 1040 | 29 | |
| 1050 | 28 | |
| 1060 | 27.5 | |
| 1070 | 27.5 | |
| 1080 | 27.5 | |
| 1090 | 27 | |
| 1100 | 26 | |
| 1110 | 26 | |
| 1120 | 26 | |
| 1130 | 26 | |
| 1140 | 25 | |
| 1150 | 24 | |
| 1160 | 25 | |
| 1170 | 23.5 | |
| 1180 | 22 | |
| 1190 | 22 | |
| 1200 | 23 | |
| 1210 | 22 | |
| 1220 | 22 | |
| 1230 | 21.5 | |
| 1240 | 19.5 | |
| 1250 | 20 | |
| 1260 | 19 | |
| 1270 | 16 | |
| 1280 | 18 | |
| 1290 | 18 | |
| 1300 | 17 | |
| 1310 | 17 | |

Fractions 550–1200 are combined, the solution is adjusted to pH 9.0, and then passed through a column containing 1 liter of IRC-50 (H+). The spent beer is collected in two fractions designated S-1 and S-2. The column is washed with 4 liters of water, 4 liters of 0.25N NH₄OH and then eluted with 1N NH₄OH. Fractions of 20 ml are collected. Testing results are as follows:

| | Zone (mm) S. lutea |
|---|---|
| Starting Material | 39 |
| S-1 | 0 |
| S-2 | 0 |
| Water | 0 |
| 0.25N NH₄OH | 0 |
| 1N NH₄OH | 0 |
| Fraction No. | |
| 10 | 0 |
| 20 | 0 |
| 90 | 0 |
| 100 | 34 |
| 110 | 40 |
| 120 | 43 |
| 130 | 43 |
| 140 | 45 |
| 150 | 46 |
| 160 | 48 |
| 170 | 48 |
| 180 | 48 |

| Fraction No. | Zone (mm) S. lutea | |
|---|---|---|
| 190 | 50 | |
| 200 | 51 | |
| 210 | 47 | |
| | | New tray |
| 220 | 51 | |
| 230 | 47 | |
| 240 | 24 | |
| 250 | 17 | |
| 260 | traces | |
| 270 | traces | |
| 280 | traces | |
| 290 | 0 | |
| 400 | 0 | |

Fractions 100–240 are combined and freeze-dried to give 4.40 grams of an essentially pure preparation of antibiotic U-48,266 which is designated Preparation ADA-87.1.

The following is a description of the purification of Preparation ADA-58.1, prepared as described above in Part C (No. 2).

The column is prepared from 600 grams of silica gel and 95% aqueous ethanol-water (75:25 v/v) as the solvent system.

The starting material, 3.0 grams of Preparation ADA-58.1, prepared as described above, is dissolved in 10 ml of water. The pH is adjusted to 10.0. Silica gel (20 grams) is then added to this solution and the mixture is concentrated to dryness. The resulting powder obtained is added on the top of the column and the column is eluted with the above-described solvent system at the rate of 9.0 ml/min. Fractions of 20 ml are obtained. Test results are as follows:

| Fraction No. | Zone (mm) S. lutea |
|---|---|
| 10 | 0 |
| 20 | 0 |
| 120 | 0 |
| 130 | 19 |
| 140 | 22 |
| 150 | 26 |
| 160 | 28 |
| 170 | 33 |
| 180 | 38 |
| 190 | 40 |
| 200 | 41 |
| 210 | 42 |
| 220 | 42 |
| 230 | 41 |
| 240 | 41 |
| 250 | 40 |
| 260 | 39 |
| 270 | 38 |
| 280 | 36 |
| 290 | 35 |
| 300 | 33 |
| 310 | 29 |
| 320 | 27 |
| 330 | 27 |
| 340 | 22 |
| 350 | 22 |
| 360 | 20 |
| 370 | 18 |
| 380 | 17 |
| 390 | traces |
| 400 | traces |
| 410 | 0 |
| 500 | 0 |

Fractions 160–350 are combined, adjusted to pH 9.0, and the solution is passed through a column prepared from 200 ml of IRC-50 (H+).

The spent is found to be bioinactive and is discarded.

The column is washed with 1 liter of water. This eluate is found to be bioactive and is also discarded.

The column is then eluted with 1 liter of 0.25N NH₄OH. This eluate is also found to be bioinactive and is also discarded. The column is then eluted with 1N NH₄OH. Fractions of 20 ml (fractions 304–400) are collected. Test results are as follows:

| Fraction No. | Zone (mm) S. lutea |
|---|---|
| 305 | 0 |
| 310 | 30 |
| 315 | 44 |
| 320 | 46 |
| 325 | 43 |
| 330 | 27 |
| 335 | 20 |
| 340 | traces |
| 345 | 0 |
| 350 | 0 |
| 355 | 0 |
| 360 | 0 |
| 365 | 0 |
| 370 | 0 |
| 400 | 0 |

Fractions 310–327 are combined and freeze-dried to give 900 mg of an essentially pure preparation of antibiotic U-48,266 which is designated ADA-71.1.

Essentially pure antibiotic U-48,266 preparations designated ADA-87.1 and ADA-71.1 are found to be identical by tlc, NMR, mass spectra and bioactivity testing against *S. lutea*.

EXAMPLE 2 - Antibiotic U-48,266 HCl

Antibiotic U-48,266 "free base", 600 mg, prepared as described in Example 1, is dissolved in a mixture of 1 ml of water, 1 ml of methanol, and 4 ml of 1N methanolic hydrogen chloride. This solution is added to 400 ml of acetone under stirring. The resulting precipitated antibiotic U-48,266 HCl is isolated by filtration and dried; yield, 700 mg.

Antibiotic U-47,929, as shown in FIG. 3 of the drawings, can be prepared according to the procedures disclosed in Example 1 of co-pending U.S. Application Ser. No. 542,226, filed on Jan. 20. 1975.

We claim:

1. Antibiotic U-48,266, which is active against *S. aureus*, *S. lutea* and *K. pneumoniae*, and which in its essentially pure form:
   a. has the molecular formula $C_{17}H_{25}N_7O_5$
   b. has the following elemental analysis: C, 50.16; H, 6.19; N, 24.09; O, 19.66;
   c. has a specific rotation of $[\alpha]_D^{25} = -6.6°$ (c, 1, water);
   d. is soluble in water and lower alcohols, for example, methanol and ethanol; is relatively insoluble in ketones, halogenated or saturated hydrocarbon solvents, ethyl acetate, or other ester-type solvents;
   e. has a characteristic infrared adsorption spectrum when dissolved in a mineral oil mull as shown in FIG. 1 of the drawings;
   f. has a characteristic NMR spectrum as shown in FIG. 2 of the drawings;
   g. has a typicla tlc pattern as shown in FIG. 3 of the drawings, or acid and base addition salts thereof.

2. The hydrochloride salt of antibiotic U-48,266, the compound defined in claim 1.

* * * * *